United States Patent [19]
Reilly et al.

[11] Patent Number: 5,521,280
[45] Date of Patent: May 28, 1996

[54] REINFORCED ABSORBABLE POLYMERS

[75] Inventors: Eugene P. Reilly, Lawrenceville; Steven C. Arnold, Franklin; Angelo G. Scopelianos, Whitehouse Station, all of N.J.

[73] Assignee: Ethicon, Inc., Somerville, N.J.

[21] Appl. No.: 388,548

[22] Filed: Feb. 14, 1995

Related U.S. Application Data

[60] Division of Ser. No. 208,391, Mar. 8, 1994, Pat. No. 5,397,816, which is a continuation-in-part of Ser. No. 977,333, Nov. 17, 1992, abandoned.

[51] Int. Cl.$^6$ .......................... C08G 64/00; A61B 17/08; C08F 283/04
[52] U.S. Cl. .......................... 528/370; 525/417; 606/151; 606/154; 606/230; 424/422
[58] Field of Search .................................. 606/151, 154; 528/370; 525/417

[56] References Cited

U.S. PATENT DOCUMENTS

| | | | |
|---|---|---|---|
| 4,052,988 | 10/1977 | Namassivaya et al. | 128/335.5 |
| 4,279,249 | 7/1981 | Vert et al. | 525/415 |
| 4,473,670 | 9/1984 | Kessidis | 523/105 |
| 4,612,923 | 9/1986 | Kronenthal | 128/92 R |
| 4,646,741 | 3/1987 | Smith | 128/334 R |
| 4,741,337 | 5/1988 | Smith et al. | 128/334 R |
| 4,743,257 | 5/1988 | Tomala et al. | 525/411 |
| 4,888,398 | 12/1989 | Bichen et al. | 525/420 |
| 5,137,928 | 9/1992 | Erbel et al. | 528/170 |
| 5,152,781 | 10/1992 | Tang et al. | 528/354 |
| 5,175,285 | 12/1992 | Lehman et al. | 544/141 |
| 5,286,810 | 2/1994 | Wood | 525/421 |
| 5,412,068 | 5/1995 | Tang et al. | 606/230 |

OTHER PUBLICATIONS

S. W. Fox, J. E. Johnson, & M. Middleebrook, J. Am. Chem. Soc., 77, 1048 (1955).
A. Vegotsky, K. Harada, & S. W. Fox, J. Am. Chem. Soc., 80, 3361 (1958).
K. Harada, J. Org. Chem., 24, 1662 (1959).
P. Neri & G. Antoni, Macromol. Synth., 8, 25 (1982).

*Primary Examiner*—Tae Yoon
*Attorney, Agent, or Firm*—Hal Brent Woodrow

[57] ABSTRACT

A composition of an absorbable polymer and a filler to increase the stiffness of the polymer is disclosed. The filler is a poly[succinimide], which is a bioabsorbable polymer that degrades into a nontoxic, simple amino acid. The composition can be melt processed to prepare medical and surgical devices, particularly those devices which are designed to penetrate bodily tissue or to withstand heavy loads. Typical surgical devices which can be made from the composition include surgical staples and ligating clips.

9 Claims, No Drawings

REINFORCED ABSORBABLE POLYMERS

BACKGROUND OF THE INVENTION

This is a division of application Ser. No. 08/208,391, filed Mar. 8, 1994, now U.S. Pat. No. 5,397,816, which is hereby incorporated by reference which is a continuation-in-part of Ser. No. 07/977,333 filed Nov. 17, 1992, now abandoned which is incorporated herein by reference.

This invention relates to compositions of absorbable polymers containing a bioabsorbable filler. More specifically, it relates to absorbable polymer compositions containing a reinforcing filler which enhances the stiffness of the polymer composition, yet decomposes into components which are biocompatible with bodily tissue.

The need to replace surgical and medical devices made of metallic components continues to grow as surgical procedures become more intricate and complex. The driving force for the replacement of such metallic devices is the need for devices composed of materials which are capable of being absorbed by the body. Bioabsorbable materials obviously represent a significant advantage over metallic materials, in that bioabsorbable materials do not need to be removed after their surgical function has been accomplished. In contrast, metallic devices remain in the body and often require removal when the surgical repair is completed to prevent possible adverse reactions occurring due to the prolonged contact of the metallic device and the surrounding bodily tissue or due to the byproducts of the corrosion of the metal.

As a result of the burgeoning need for bioabsorbable materials in surgery and for other medical applications, a body of art has been developed which utilizes bioabsorbable polymers as the structural component of these devices. In this manner, once the device has performed its function, the bioabsorbable polymer from which it is composed readily breaks down into nontoxic segments which can be metabolized or passed through bodily tissue. For example, U.S. Pat. No. 4,052,988 describes preparing absorbable surgical devices from polymers of 1,4-dioxanone and 1,4-dioxepan-2-one. The devices which can be prepared from these absorbable polymers include sutures, tubular implants, surgical meshes, staples, and cylindrical pins, rods or screws. The properties of the polymers from which the devices are made can be changed by copolymerizing 1,4-dioxanone or 1,4-dioxepan-2-one with other lactone monomers, such as lactide or glycolide, or by forming mixtures of the homopolymers with other absorbable polymers.

Other examples exist of the use of bioabsorbable polymers as the main component for surgical devices. U.S. Pat. No. 4,741,337 describes surgical fasteners, particularly staples, composed of a polymeric blend derived from homopolymers and copolymers of lactide and glycolide. The blending of the polymers is optimized to yield fasteners which can retain their strength in vivo for prolonged time periods, yet become impalpable shortly thereafter.

Another example of surgical devices made from absorbable polymers can be found in U.S. Pat. No. 4,646,741. This patent describes surgical fasteners made from polymeric blends. The blends contain a copolymer of lactide and glycolide and a homopolymer of 1,4-dioxanone. Once again, the proportion of polymers in the blend is carefully controlled to achieve the optimum properties for the fastener.

While absorbable, polymeric surgical and medical devices represent an advantage over metallic devices because the polymeric devices do not need to be removed from the body, such polymeric devices often have a major drawback which has limited their applications. Specifically, absorbable polymers typically lack the strength and stiffness of metallic components. Strength is an important asset for devices designed to penetrate bodily tissue or to withstand heavy loads. For these applications, the absorbable polymers must be stiff enough to withstand the penetration forces or the load placed on them. With respect to this important attribute of stiffness, absorbable polymers are usually incapable of matching the performance characteristics of metals and metal alloys used for surgical devices.

Accordingly, attempts have been made to increase the stiffness of bioabsorbable polymers from which surgical and medical devices are made. U.S. Pat. No. 4,473,670 describes preparing absorbable polymers containing finely divided sodium chloride or potassium chloride for surgical devices such as ligating clips and staples. The salt filler enhances certain properties of the polymer, most notably its stiffness. The absorbable polymers which can be used include homopolymers and copolymers of lactide, glycolide, and 1,4-dioxanone. In a similar manner, U.S. Pat. No. 4,612,923 discloses another example of using a filler to increase the stiffness of an absorbable polymer. In this case, an absorbable glass is used as the filler.

Unfortunately, the use of bioabsorbable glasses or inorganic salts as fillers for bioabsorbable polymers has certain disadvantages. First, since the absorbable polymer matrix is organic material, and the fillers described in these patents are inorganic compounds, the adhesion between the absorbable polymer matrix and the filler may be less than desirable for adequate performance. That is, a lack of adhesion between the filler and the polymer matrix will tend to reduce the synergistic effects of their combination, and significant improvements in stiffness may not be realized. Second, the use of an absorbable glass filler may cause the calcification of soft tissue when the device from which the glass filled polymer degrades inside the body.

In view of the deficiencies of the prior art, what is needed is a bioabsorbable filler for absorbable polymers in which the filler can readily break down into biocompatible segments. In addition, and most importantly, what is also needed is an organic compound that is used as a reinforcing filler and is compatible with the absorbable polymer matrix so that good adhesion and blending can be established for the optimum improvement in the properties, especially the stiffness of the polymer.

SUMMARY OF THE INVENTION

The invention is a composition comprising an absorbable polymer capable of being absorbed by the body. The polymer contains as a filler a poly[succinimide] in an amount sufficient to increase the stiffness of the polymer.

Surprisingly, the poly[succinimide] filler increases the stiffness of an injection molded device made of an absorbable polymer as measured by the Young's modulus of that device in comparison to an injection molded part which does not contain the poly[succinimide] filler. Poly[succinimide] biodegrades into a nontoxic, simple amino acid, which can readily be eliminated in the body.

Contrary to the use of absorbable glasses as fillers for absorbable polymers, there is no calcification of tissues when poly[succinimide] is used as the filler for the polymer. Additionally, poly[succinimide] is an organic polymer which, unlike the inorganic fillers described in the art, is compatible with the absorbable polymer matrix. In this manner, the adhesion between the absorbable polymer and poly[succinimide] filler is greater than that which would be achieved between the absorbable polymer and the inorganic glass or salt fillers. Moreover, this inherently good adhesion between the polymer matrix and the poly[succinimide] filler may be improved by surface treatments prior to the blending operation. Therefore, significant increases in the stiffness of the absorbable polymer composition can be achieved by incorporating the organic, poly[succinimide] filler into the absorbable polymer composition.

Finally, poly[succinimide] is an amorphous polymer which has a very high glass transition temperature of about 200° C. The significance of this property is that the polysuccinimide does not soften or react when it is incorporated into the absorbable polymer composition at processing temperatures below its glass transition temperature. Thus, the poly[succinimide] filler is easy to process and successfully incorporate into the absorbable polymer composition to improve the stiffness of the polymer.

The compositions of this invention can be used for any application in which such compositions can be envisioned, but they are especially useful for the preparation of medical and surgical devices.

DETAILED DESCRIPTION OF THE INVENTION

Poly[succinimides] are known polymeric compounds, and the synthesis of poly[succinimide] by the thermal polymerization of aspartic acid is reported in the following references: S. W. Fox, J. E. Johnson, and M. Middlebrook, J. Am. Chem. Soc., 77, 1048 (1955); J. Kovacs, I. Koenyves, and A. Pusztai, Experientia, 9, 459 (1959); J. Kovacs and I. Koenyves, Naturwiss, 41, 333 (1953); A. Vegotsky, K. Harada, and S. W. Fox, J. Am. Chem. Soc., 80, 3361 (1958); K. Harada, J. Org. Chem., 24, 1662 (1959). An improved synthesis of poly[succinimide] was published and involved the polycondensation of D,L-aspartic acid using 85 weight percent phosphoric acid. See P. Neri and G. Antoni, Macromol. Synth., 8, 25 (1982).

For the purpose of defining this invention, a poly[succinimide] is any polymer derived from aspartic acid, aspartic acid anhydride, or any substituted equivalent of aspartic acid or aspartic acid anhydride, including all possible combinations of stereoisomers of these compounds. In addition, a poly[succinimide] is any polymerization reaction product which would yield the structural equivalent of any of the polymers described in the preceding sentence. The most preferred poly[succinimide] is a polymer which has repeating units represented by the following chemical formula:

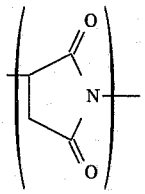

A polymer is "absorbable" within the meaning of this invention if it is capable of breaking down into small, nontoxic segments which can be metabolized or eliminated from the body without harm. Generally, absorbable polymers swell, hydrolyze, and degrade upon exposure to bodily tissue, resulting in a significant weight loss. The hydrolysis reaction may be enzymatically catalyzed in some cases. Complete bioabsorption, i.e. complete weight loss, may take some time, although preferably complete bioabsorption occurs within 12 months, most preferably within 6 months.

The absorbable polymer may be a naturally occurring polymer, such as a bacterial polyester, or a synthetic polymer. Suitable synthetic absorbable polymers include polymers selected from the group consisting of aliphatic polyanhydrides (described in U.S. Pat. No. 4,757,128 incorporated by reference herein), aromatic polyanhydrides (described in U.S. Pat. No. 5,264,540 incorporated by reference herein), radiation stable polylactones (described in U.S. Pat. Nos. 4,435,590, 4,510,295, 4,532,928 and 4,689,424 incorporated by reference herein), poly(esteranhydrides) (as described in patent application Ser. No. 03/062,865 filed May 14, 1993 and assigned to Ethicon, Inc.), polyiminocarbonates, polyesters made by step growth polymerization, especially polyesters that are absorbable like those made from oxalic (described in U.S. Pat. No. 4,141,087 incorporated by reference herein), malic, or tartaric acids, polyamides made by step growth or ring opening polymerization, nontoxic structural poly(aminoacids) or polypeptides made by the ring opening polymerization of N-carboxyanhydrides or by genetic engineering, poly(hydroxybutyrate), poly(hydroxybutyrate-co-hydroxyvalerate), other bacterially derived polyesters (described in Lenz, etal. Macromolecules 22, 1106 (1989); 23 5059 (1990); 24 5256 (1991); 25 1852 (1992), polyphosphazenes, polyesteramides like polymorpholinediones (described in U.S. Pat. Nos. 4,441,496 and 4,916,209 incorporated by reference herein), and block copolymers of polyethylene glycol and polylactones (described in U.S. Pat. No. 4,452,973 incorporated by reference herein). Preferably, the absorbable polymer is a synthetic polymer. The preferred synthetic absorbable polymers are derived from the class of monomers generally referred to in the art as lactone monomers (including acid equivalents of these monomers that may be used to form absorbable polymers). Examples of lactone monomers include glycolide, lactide, 1,4-dioxanone, trimethylene carbonate, δ-valerolactone, ε-caprolactone, 1,4-dioxepan-2-one, 1,5-dioxepan-2-one, and substituted equivalents of these compounds as well as the cyclic dimers of these compounds.

Also envisioned within the scope of the invention are compositions composed of copolymers of the above-mentioned lactone monomers. Random, block or graft copolymers of any of the lactone monomers can be prepared to make compositions which fall within the scope of this invention. In a similar manner, polymeric blends can be used, in which absorbable polymers are blended to prepare a mixture of the individual polymer components.

The preferred absorbable polymers are synthetic polymers derived from the polymerization of lactide, glycolide and 1,4-dioxanone. The most preferred polymers are the homopolymer of 1,4-dioxanone and copolymers of lactide and glycolide. It is advantageous that the polymer have a molecular weight which is sufficient for melt processing to prepare surgical or medical devices.

The amount of poly[succinimide] filler which is sufficient to increase the stiffness of the polymer will depend on numerous factors, including the particular polymer chosen and the application for which the polymer composition is used. The amount to increase the stiffness can be readily determined empirically. However, as a general rule, the concentration of the poly[succinimide] filler in the polymer can vary over a range from about 10 to about 80 percent of the weight of the filled composition. Preferably, from about 20 to about 40 weight percent of the poly[succinimide] filler is used. If the concentration were less than about 10 weight percent of filler, then the desired increase in stiffness of the polymer may not be realized. Conversely, if the concentration of filler were greater than about 80 weight percent, then the processability of the composite may be compromised.

The filler may be in any structural form which is suitable for the equipment being used to prepare the composition and which is necessary to achieve the desired final properties. For example, the poly[succinimide] filler may be a powder, or it could be in the form of continuous or staple fibers. It may also be in the form of microfibers, whiskers, or plates. Fibers may be the preferred form when uniaxial or biaxial orientation in the polymer composition is desired. The greatest increases in mechanical properties are achieved when the filler has a high aspect ratio. On the other hand, a powder may be preferred when a uniform distribution of the filler in the polymer matrix is desired. If processability is the primary concern, then the filler is preferably in the form of a finely divided powder. Such a finely divided powder is often easiest to uniformly distribute throughout the polymer.

If a finely divided powder is used as the poly[succinimide] filler, then the particle size distribution of the powder can vary over a wide range, but it is typically preferred to have a particle size distribution ranging from about 50 to about 150 microns. However, even particle sizes under about 50 microns can be used to stiffen the absorbable polymer. Poly[succinimides] are isolated and purified by precipitation. Precipitation techniques may be used to control the size and to some extent the shape of the poly[succinimide] filler. Generally, when a finely divided powder is required, the precipitated poly[succinimide] is ground and sifted through sieves to yield a relatively uniform particle size distribution. A uniform distribution of these poly[succinimide] particles in the polymer matrix is also desired to achieve the optimum properties.

The incorporation of the poly[succinimide] filler into the absorbable polymer can be accomplished using conventional methods. Preferably, when a finely divided powder is used as the filler, the poly[succinimide] powder is dried, ground, and sifted through appropriate micron sieves until a sufficient quantity of the particles of desired size distribution is produced. The screened particles are desirably kept dry by storage under vacuum until they can be dry blended with the absorbable polymer in an appropriate mixer. The mixing operation should be performed until a uniform dispersion of the poly[succinimide] particles in the polymer is achieved. If the poly[succinimide] is used in the form of continuous or staple fibers, then conventional techniques for the processing of fibrous products can be used.

The poly[succinimide] filler may also be added to the monomer feed at the time of the polymerization of the monomer or comonomers provided that adequate mixing is used.

Once the compositions of this invention are made, they can be easily processed using conventional melt processing techniques to prepare numerous medical and surgical devices. The compositions can be extruded to prepare fibers for sutures and ligatures. Preferably, the compositions are injection molded to prepare a vast array of devices which are designed to penetrate bodily tissue or to withstand heavy loads. Included among such devices are surgical staples and ligating clips.

The following examples are intended to illustrate the preferred embodiments of this invention. By no means should these examples be construed to limit the scope and spirit of this invention as it is delineated in the appended claims. Numerous additional embodiments will become readily apparent to those skilled in this art.

EXAMPLES

EXAMPLE 1

PREPARATION OF POLY[SUCCINIMIDE] FROM D,L-ASPARTIC ACID 200.4 Grams (1.50 moles) of D,L-aspartic acid and 101.2 grams (0.878 moles) of an 85 weight percent aqueous phosphoric acid solution were placed into a three liter, three neck, round bottom flask equipped with a mechanical stirrer, a nitrogen gas inlet with a Firestone valve, and a vent. This suspension was heated with an oil bath to 200° C. The mixture began to boil, and the steam was carried out of the reaction flask by the stream of nitrogen. After fifteen to thirty minutes, a vacuum hose with a pinch clamp was connected to the vent, and a vacuum was slowly applied by opening the pinch clamp in stages. The nitrogen gas was turned off during the vacuum distillation. Foaming was a problem as the pressure in the reaction chamber was reduced. Foaming was controlled by carefully adjusting the pressure. Full vacuum was usually obtained after forty five to sixty minutes. The reaction mixture was held under high vacuum at 200° C. for two hours, and then, allowed to cool down to room temperature under nitrogen.

1.5 Liters of dimethylformamide (DMF) were added to the reaction flask, and the resulting mixture was heated to 150° C. until all of the poly[succinimide] had dissolved. The solution was transferred into a large stainless steel blender and stirred vigorously while 3.75 liters of distilled water were added. The tan powder was isolated by suction filtration, washed with several liters of distilled water, and finally washed with one liter of methanol. The filtercake was air dried on the Büchner funnel and vacuum dried at 110° C. for twenty four hours. The vacuum trap was cleaned periodically during the devolatization cycle.

138 Grams of a light tan powder of poly[succinimide] were collected. The inherent viscosity was 0.23 dL/g in DMF at 25° C. (c=0.10 g/dL). FTIR (KBr pellet, cm$^{-1}$): 3490 (broad), 2954, 1801, 1714, 1389, 1363, 1288, 1257, 1214, 1162, 935, 700, 636. $^1$H NMR (300 MHz, d$_7$-DMF, ppm) δ 2.85 [bs, 1H], 3.35 [bs, 1H], 5.5 [broad two lines, 1H]. The glass transition temperature was 200° C. as measured by differential scanning calorimetry (DSC) at 20° C. per minute under nitrogen.

EXAMPLE 2

PREPARATION OF POLY[SUCCINIMIDE] FROM D-ASPARTIC ACID 50.0 Grams (0.376 moles) of D-aspartic acid and 25.3 grams (0.219 moles) of an 85 weight percent aqueous phosphoric acid solution were placed into a 500 mL, three neck, round bottom flask equipped with a mechanical stirrer, a distillation head, and a collection flask. The reaction flask was immersed in an oil bath and connected to both a nitrogen gas line and a vacuum line with a Firestone valve. The suspension was heated with an oil bath to 200° C. under an inert atmosphere. The mixture began to boil, and water was collected. The collection flask was chilled with dry ice. Some foaming occurred and the viscosity of the reaction mixture increased. After about one hour, mechanical stirring was stopped and a vacumm was slowly applied to the reaction mixture. Water continued to distill out. Foaming was not a serious problem. The reaction mixture was held at 200° C. for two hours under high vacuum and then allowed to cool down to room temperature under nitrogen.

275 Milliliters of DMF were added to the reaction flask, and the resulting mixture was heated to 150° C. until all of the poly[succinimide] had dissolved. The solution was transferred into a 500 mL separatory funnel and added into a large stainless steel blender containing two liters of distilled water with vigorous stirring. A tan powder precipitated out of solution and was isolated by suction filtration. The filtercake was washed with several liters of distilled water and then with about 500 mL of methanol, and air dried on the B üchner funnel. The wet filtercake was a tan paste and weighed 169.3 grams, was transferred into a dish, and finally vacuum dried at 110° C. for twenty four hours. The vacuum trap was cleaned periodically during this devolatization step. 35.6 grams of a tan material were isolated and ground into a fine power in a mortar and pestle. The inherent viscosity of this poly[succinimide] was 0.39 dL/g in DMF at 25° C. (c=0.10 g/dL). A broad endothermic transition was observed by DSC between 200° C. and 300° C. Thermal decomposition started to occur around 390° C. as determined by thermogravimetric analysis (TGA). The poly[succinimide] lost about 3.90 weight percent by the onset of decomposition.

EXAMPLE 3

PREPARATION OF POLY[SUCCINIMIDE] FROM L-ASPARTIC ACID 50.0 Grams (0.376 moles) of L-aspartic acid and 25.3 grams (0.219 moles) of an 85 weight percent aqueous phosphoric acid solution were placed into a 500 mL, three neck, round bottom flask equipped with a mechanical stirrer, a distillation head, and a collection flask. The reaction flask was immersed in an oil bath and connected to both a nitrogen gas line and a vacuum line with a Firestone valve. The suspension was heated with an oil bath to 200° C. under an inert atmosphere. The mixture began to boil, and water was collected. The collection flask was chilled with dry ice. Some foaming occurred and the viscosity of the reaction mixture increased. After about one hour, mechanical stirring was stopped and a vacumm was slowly applied to the reaction mixture. Water continued to distill out. Foaming was not a serious problem this time. The reaction mixture was held at 200° C. for two hours under high vacuum and then allowed to cool down to room temperature under nitrogen.

300 Milliliters of DMF were added to the reaction flask, and the resulting mixture was heated to 150° C. until all of the poly[succinimide] had dissolved. The solution was transferred into a 500 mL separatory funnel and added into a large stainless steel blender containing two liters of distilled water with vigorous stirring. A tan powder precipitated out of solution and was isolated by suction filtration. The filtercake was washed with several liters of distilled water and then with about 500 mL of methanol, and air dried on the Büchner funnel. 195 grams of wet filtercake were vacuum dried at 110° C. for twenty two hours. The vacuum trap was cleaned periodically during the devolatization process. 36.3 grams of a tan material were isolated and ground into a fine power in a mortar and pestal. The inherent viscosity of this poly[succinimide] was 0.38 dL/g in DMF at 25° C. (c=0.10 g/dL). A broad endothermic transition was observed by DSC between 200° C. and 300° C. Thermal decomposition started to occur around 390° C. as determined by TGA. The poly[succinimide] lost about 9.0 weight percent by the onset of decomposition.

EXAMPLE 4

IN VIVO ABSORPTION AND TISSUE REACTION STUDY 2.5 Grams of poly[succinimide], prepared as described in Example 1 and having an inherent viscosity of 0.29 dL/g, were dissolved in 10 mL of DMF at room temperature in a 50 mL Erlenmeyer flask. In the glove box, the resulting viscous solution was poured into a silanized dish and covered with a large beaker to slow down the evaporation of the solvent. After two weeks, the film was still soft. The beaker was then replaced by the top section of an uncapped one gallon milk jug with its bottom cut out to speed the evaporation rate. After another two weeks, a brittle amber film had formed. The film was then cut into 0.3×2.0 cm strips with a hot spatula. The edges of the strips were sanded smooth with an emery board. These poly[succinimide] strips were kept dry by storage in a vacuum oven and were later placed in packages, sterilized by ethylene oxide exposure, and sealed under nitrogen. No residual DMF was detected by 300 MHZ $^1$H NMR spectroscopy in the poly[succinimide] strips.

The sterilized strips of poly[succinimide] were evaluated for intramuscular tissue reaction and absorption in rats. The tissue reaction at three and seven days was slight to moderate. Nothing unusual was observed. The tissue reaction decreased steadily with implantation time. After 56 days, the poly[succinimide] was completely absorbed in some animals and almost completely absorbed in others. A few small fragments of polymer remained. The absorption of poly[succinimide] was checked again after 119 days, at which time it was observed that all of the poly[succinimide] had completely disappeared.

EXAMPLE 5

GRINDING AND SIFTING OF POLYSUCCINIMIDES

The batches of poly[succinimide] from Examples 2 and 3 were ground into fine powders using a mortar and pestle. Each material was sifted through a 150 micron sieve and then through a 50 micron sieve to produce 10 grams of material consisting of particle sizes ranging from 150 to 50 microns (i.e., material sifted through 150 μm sieve but not through 50 μm sieve). The ground and screened materials were stored in a vacuum oven at room temperature.

The poly[succinimide] of Example 2 was also ground using a mortar and pestle to yield 8.0 grams of material passing through a 50 micron sieve.

EXAMPLE 6

INJECTION MOLDING OF POLY[1,4-DIOXANONE] BARBELLS

Cylindrical barbells were molded from poly[1,4-dioxanone] having an inherent viscosity of 1.8 dL/g in hexafluoroisopropanol at 30° C. (c=0.10 g/dL) on a benchtop injection molding machine (manufactured by Custom Scientific Instruments, Mini Max Molder Model CS-182MMX). These barbells were molded between 120° C. and 130° C.; the residence time in the Mini Max Molder was approximately three minutes; and the barbells did not adhere to the mold. The barbells were annealed at 85° C. for 18 hours under a nitrogen atmosphere.

EXAMPLE 7

INJECTION MOLDING OF POLY[1,4-DIOXANONE] BARBELLS AFTER BEING KNEADED IN A BRABENDER PLASTI-CORDER

The same batch of poly[1,4-dioxanone] used in Example 6 (I.V.=1.8 dL/g) was placed in the small mixing bowl of a Brabender Plasti-Corder (Model PL 2000) equipped with roller blades and heated at 130° C. for thirty minutes with the blades turning at five revolutions per minute. Then, the mixing bowl was disassembled, and the polymer removed. The poly[1,4-dioxanone] was stored in the dark under vacuum prior to grinding. The polymer was frozen in liquid nitrogen and ground in a Wiley mill to pass through a 6mm screen. The resulting course ground resin of poly[1,4-dioxanone] was stored under vacuum for at least 24 hours prior to injection molding. Cylindrical barbells of this kneaded poly[1,4-dioxanone] were molded and annealed as described in Example 6.

EXAMPLE 8

INJECTION MOLDING OF POLY[1,4-DIOXANONE] BARBELLS AFTER BEING KNEADED IN THE BRABENDER EXTRUDER

Example 7 was repeated. This example is just another control experiment performed at the time the smaller particle size blend was prepared and molded.

EXAMPLE 9

INJECTION MOLDING OF POLY[SUCCINIMIDE] FILLED POLY[1,4-DIOXANONE] BARBELLS 9.0 Grams of the 150-50 micron particle size poly[succinimide], made in Example 2 and sifted in Example 5, were combined with 21.0 grams of poly[1,4-dioxanone] having an inherent viscosity of 1.8 dL/g in a jar and shaken by hand for a few minutes. The mixture was then added to the small mixing bowl of a Brabender PlastiCorder at 130° C. and blended for thirty minutes with the blades turning at five revolutions per minute. The mixing bowl was disassembled, and the blend was removed. The poly[succinimide] filled poly[1,4-dioxanone] blend was stored in the dark under vacuum. The blend was frozen in liquid nitrogen and ground in a Wiley mill to pass through a 6 mm screen. After grinding, the samples were stored under vacuum for at least 24 hours prior to injection molding.

Cylindrical barbells of this poly[succinimide] filled poly [1,4-dioxanone] blend were molded on a Mini Max benchtop injection molding machine between 150° C. and 170° C. in order to fill the mold completely, whereas the unfilled poly[1,4-dioxanone] was molded between 120° C. and 130° C. The residence time in the Mini Max was approximately three minutes, and the barbells did not adhere to the mold. The resulting barbells were placed in a glass dish and were annealed at 85° C. for 18 hours under a nitrogen atmosphere.

EXAMPLE 10

INJECTION MOLDING OF POLY[SUCCINIMIDE] FILLED POLY[1,4-DIOXANONE] BARBELLS 9.0 Grams of the 150-50 micron particle size poly[succinimide], made in Example 3 and sifted in Example 5, were combined with 21.0 grams of poly[1,4-dioxanone] having an inherent viscosity of 1.8 dL/g in a jar and shaken by hand for a few minutes. The mixture was then added to the small mixing bowl of a Brabender PlastiCorder at 130° C. and blended for thirty minutes with the blades turning at five revolutions per minute. The mixing bowl was disassembled, and the blend was removed. The poly[succinimide] filled poly[1,4-dioxanone] blend was stored in the dark under vacuum. The blend was frozen in liquid nitrogen and ground in a Wiley mill to pass through a 6 mm screen. After grinding, the samples were stored under vacuum for at least 24 hours prior to injection molding.

Cylindrical barbells of this poly[succinimide] filled poly [1,4-dioxanone] blend were molded on a Mini Max benchtop injection molding machine between 150° C. and 170° C. The residence time in the Mini Max was approximately three minutes, and the barbells did not adhere to the mold. The resulting barbells were placed on a glass dish were annealed at 85° C. for 18 hours under a nitrogen atmosphere.

EXAMPLE 11

INJECTION MOLDING OF POLY[SUCCINIMIDE] FILLED POLY[1,4-DIOXANONE] BARBELLS 8.0 Grams of the 50 micron or less particle size poly [succinimide], made in Example 2 and sifted in Example 5, were added to 18.6 grams of poly[1,4-dioxanone] having an inherent viscosity of 1.8 dL/g in a jar and shaken by hand for a few minutes. The mixture was then added to the small mixing bowl of a Brabender Plasti-Corder at 130° C. and blended for thirty minutes with the blades turning at five revolutions per minute. The mixing bowl was disassembled, and the blend was removed. The poly[succinimide] filled poly[1,4-dioxanone] blend was stored in the dark under vacuum. The blend was frozen in liquid nitrogen and ground in a Wiley mill to pass through a 6 mm screen. After grinding, the samples were stored under vacuum for at least 24 hours prior to injection molding.

Cylindrical barbells of this polysuccinimide filled poly[1, 4-dioxanone] blend were molded on a Mini Max benchtop injection molding machine between 150° C. and 170° C. The residence time in the Mini Max was approximately three minutes, and the barbells were placed in a glass dish did not adhere to the mold. The resulting barbells were placed in a glass dish and were annealed at 85° C. for 18 hours under a nitrogen atmosphere.

EXAMPLE 12

TENSILE TESTING OF THE BARBELLS

The tensile properties of the cylindrical barbells of poly [1,4-dioxanone] and of the poly[succinimide] filled poly[1, 4-dioxanone] blends are shown in Tables I and II for the two different particle size fillers.

TABLE I

Poly[succinimide] Filled Poly[1,4-dioxanone]
(150-50 Micron Particle Size)
Tensile Properties

| Example Number | Yield Strength (psi) | Yield Strain (%) | Breaking Strength (psi) | Strain at Break (%) | Young's Modulus (ksi) | Percent Modulus Increase |
|---|---|---|---|---|---|---|
| Ex. 6 Control | 6700 | 23 | 6130 | 34 | 54 | NA |
| S.D. | 370 | 2 | 390 | 5 | 6 | |
| Ex. 7 Kneaded Control | 7080 | 21 | 4520 | 57 | 48 | NA |
| S.D. | 300 | 4 | 800 | 44 | 5 | |
| Ex. 9 30 wt. % Filler | 8270 | 14 | 7220 | 25 | 77 | 60 |
| S.D. | 370 | 1 | 590 | 4 | 6 | |
| Ex. 10 30 wt. % Filler | 7700 | 13 | 7250 | 16 | 76 | 58 |
| S.D. | 160 | 1 | 310 | 1 | 9 | |

S.D. means standard deviation.

TABLE II

Poly[succinimide] Filled Poly[p-dioxanone]
(50 Microns and less Particle Size)
Tensile Properties

| Example Number | Yield Strength (psi) | Yield Strain (%) | Breaking Strength (psi) | Strain at Break (%) | Young's Modulus (ksi) | Percent Modulus Increase |
|---|---|---|---|---|---|---|
| Ex. 6 | 6700 | 23 | 6130 | 34 | 54 | NA |
| Ex. 8 Kneaded Control | 7320 | 19 | 5140 | 74 | 50 | NA |
| S.D. | 430 | 2 | 1000 | 53 | 10 | |
| Ex. 11 30 wt. % Filler | 7320 | 15 | 6540 | 25 | 69 | 38 |
| S.D. | 290 | 1 | 415 | 4 | 5 | |

S.D. means standard deviation.

Two poly[1,4-dioxanone] controls were employed. The first control (Example 6) was simply the poly[1,4-dioxanone] used in all of the experiments, having an inherent viscosity of 1.8 dL/g. This material was injection molded at 120° C. into barbells which were then annealed and tensile tested. The second poly[1,4-dioxanone] controls (Examples 7 and 8) were injection molded after being melted and kneaded in the Brabender Plastic-Corder in the same way that the poly[succinimide] filled poly[1,4-dioxanone] blends were prepared. As shown in the first two rows of Table I, barbells of the unkneaded and kneaded poly[1,4-dioxanone] had virtually the same mechanical properties, indicating that the melt blending process used in this study did not alter the poly[1,4-dioxanone] to any appreciable extent.

Two poly[succinimide] filled poly[1,4-dioxanone] blends (Examples 9 and 10) were prepared using two different batches of poly[succinimide] (Examples 2 and 3) of similar molecular weight having a particle size between 150 and 50 microns. These blends contained 30 weight percent poly[succinimide]. The tensile properties of these filled systems are shown in the last two rows of Table I and are almost identical. The Young's modulus of the poly[succinimide] filled poly[1,4-dioxanone] increased about 60 percent over that of the unfilled poly[1,4-dioxanone], and the elongation to break decreased. Furthermore, the tensile strength of the poly[succinimide] filled poly[1,4-dioxanone] was slightly higher than that of the unfilled poly[1,4-dioxanone] which suggests that the poly[succinimide] filler is evenly dispersed and has reasonably good adhesion to the poly[1,4-dioxanone] matrix.

Similarly, as listed in Table II, barbells made from the blend of poly[1,4-dioxanone] and poly[succinimide] consisting of particles of 50 microns or less (Example 11) showed a 38 percent increase in the Young's modulus over that of virgin poly[1,4-dioxanone] barbells (Example 8).

We claim:

1. A surgical device comprising an absorbable matrix comprising an absorbable polymer selected from the group consisting of aliphatic polyanhydrides, aromatic polyanhydrides polylactones homopolymers, polylactone copolymers, poly(esteranhydrides), polyiminocarbonates, polyesters of oxalic acid, polyesters of malic acid, polyesters of tartaric acid, polyamides, poly(aminoacids), nontoxic polypeptides, poly(hydroxybutyrate), poly(hydroxybutyrate-co-hydroxyvalerate), bacterially derived polyesters, polyphosphazenes, polyesteramides and block copolymers of polyethylene glycol and polylactones capable of being absorbed by the body containing as a discrete filler material, a poly[succinimide], in an amount sufficient to increase the stiffness of the polymer, having repeating units represented by the following formula:

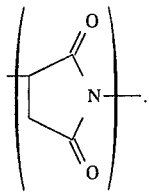

2. The device of claim 1 wherein the device is a surgical staple.

3. The device of claim 1 wherein the device is a ligating clip.

4. The device of claim 1 wherein the synthetic absorbable polymer is derived from at least one lactone monomer.

5. The device of claim 4 wherein the lactone monomer is selected from the group consisting of lactide, glycolide, 1,4-dioxanone, trimethylene carbonate, δ-valerolactone, ε-caprolactone, 1,4-dioxepan-2-one, 1,5-dioxepan-2-one, cyclic dimers thereof and combinations of two or more thereof.

6. The device of claim 4 wherein the absorbable polymer is selected from the group consisting of homopolymers of 1,4-dioxanone and copolymers of lactide and glycolide.

7. The device of claim 6 wherein the absorbable polymer is a homopolymer of 1,4-dioxanone.

8. The device of claim 1 wherein the amount of the poly[succinimide] filler in the absorbable polymer is between about 10 to about 80 percent of the weight of the composition.

9. The device of claim 1 wherein the amount of the poly[succinimide] filler in the absorbable polymer is between about 20 to about 40 percent of the weight of the composition.

\* \* \* \* \*